United States Patent [19]

Shimmick et al.

[11] Patent Number: 5,339,121
[45] Date of Patent: Aug. 16, 1994

[54] RECTILINEAR PHOTOKERATOSCOPE

[75] Inventors: John Shimmick, Redwood City; Charles R. Munnerlyn, Sunnyvale, both of Calif.

[73] Assignee: Visx, Incorporated, Santa Clara, Calif.

[21] Appl. No.: 786,650

[22] Filed: Nov. 1, 1991

[51] Int. Cl.⁵ ............................................. A61B 3/10
[52] U.S. Cl. .................................. 351/212; 351/246; 351/247
[58] Field of Search ................ 351/211, 212, 247, 246

[56] References Cited

U.S. PATENT DOCUMENTS 3,169,459  2/1965  Friedberg et al. .
3,756,702  9/1973  Trachtman .
4,355,871  10/1982 Nevyas et al. .
4,398,812  8/1983  Kelman .
4,490,022  12/1984 Reynolds .
4,685,140  8/1987  Mount, II .
4,820,039  4/1989  Ahmad .
4,863,260  9/1989  Gersten et al. .

Primary Examiner—William L. Sikes
Assistant Examiner—Hung Xuan Dang
Attorney, Agent, or Firm—Graham & James

[57] ABSTRACT

A rectilinear keratoscope for determining the curvature of the anterior corneal surface of an eye. The keratoscope includes a translucent sheet having a curved pattern in the shape of a grid of intersecting individual curved lines. The pattern forms a substantially rectilinear grid image when reflected from a curved surface having a known radius of curvature. Deviations from a spherical surface can be qualitatively and quantitatively determined from examining the nature of the reflected image pattern and by measuring the spatial frequency of grid lines lying between a reference point and an image point corresponding to a point on the surface of the cornea whose refractive power is to be measured.

8 Claims, 3 Drawing Sheets

RECTILINEAR PHOTOKERATOSCOPE

BACKGROUND OF THE INVENTION

This invention relates to devices used to measure the curvature of the anterior corneal surface.

The curvature of the anterior corneal surface is of interest in a number of disciplines. For example, in the course of performing surgical procedures on the eye, such as photorefractive keratectomy, the anterior surface of the cornea is modified in order to improve the refractive characteristics of the human eye (i.e., to correct for refractive errors). In the field of contact lens fitting, it is desirable to map the anterior corneal surface so that the posterior surface of the contact lens can be more precisely fitted in order to improve lens performance and reduce eye irritation. Of particular interest in mapping the anterior corneal surface is the curvature of that surface. Attempts to measure this curvature have centered about the technique of reflecting patterns from the surface using optical apparatus with patterns of different types, including bars, squares and, currently, concentric circles or circular segments termed placido rings (mires). Examples of such devices are described in U.S. Pat. No. 4,490,022 for "Apparatus for Corneal Corrective Techniques"; U.S. Pat. No. 4,685,140 for "Keratograph Auto Scanner System"; and U.S. Pat. No. 4,820,039 entitled "Medical Apparatus for Diagnosing Eye Conditions", the disclosures of which are hereby incorporated by reference.

Generally, the preselected pattern, which currently preferably constitutes placido rings, is reflected from the anterior corneal surface and captured either on film or as an electronic video image. After the image is captured, it is analyzed using various techniques to afford both qualitative and quantitative analysis of the corneal surface curvature. The curvature, in turn, can be related to the refractive power of the anterior corneal surface at given points of interest.

While known techniques for analyzing the curvature of the anterior surface of the cornea have been found to be useful, there are certain disadvantages. For example, the curvature analyses in many known systems are made with reference to the vertex of the corneal surface, sometimes termed the central reflex. This point, however, is typically displaced from the actual center of the pupil, from which the measurements should ideally be taken. In addition, the known technique using placido rings is difficult to relate to abrupt changes in the surface curvature. Also, the repeatability of results with many existing systems is on the order of 0.5 diopter, which is less than desirable.

SUMMARY OF THE INVENTION

The invention comprises a method and apparatus for providing a highly useful patterned image of the anterior surface of the cornea, which can be used to provide more accurate qualitative and quantitative analysis of the surface curvature.

From an apparatus aspect, the invention comprises a grid element for use in a keratoscope to determine the curvature of the anterior corneal surface of an eye. The grid element comprises a member having a curved pattern formed thereon, the pattern having the property of forming a substantially rectilinear grid image when reflected from a curved surface having a radius of curvature lying wihtin a predetermined range. The curved pattern preferably comprises a grid of intersecting individual lines centered about the origin of the pattern so that the image of the central portion of the eye is unobstructed when the grid is placed in a keratoscope and the eye is viewed along the optical axis of the device. The grid is preferably formed by milling the curved line pattern into one side of a translucent sheet of material, and highlighting the pattern with a suitable contrasting substance such as white paint or some other light scattering substance.

From a method standpoint, the invention comprises a technique for determining the curvature of a corneal surface including the steps of providing a grid of lines having a pattern which forms an image comprising a substantially rectangular grid when reflected from a curved surface having a radius of curvature lying wihtin a predetermined range, placing the grid before the anterior corneal surface of an eye, and capturing the image of the grid reflected from the corneal surface. The curvature of the anterior corneal surface can be determined qualitatively by inspecting the reflected grid pattern and observing the nature of the lines. In particular, broken lines indicate sharp discontinuities in the curvature of the corneal surface, while wavy lines signify gradual transition areas. The refractive power of any point on the anterior corneal surface can be calculated from the captured image by measuring the spatial frequency of grid lines between a reference point and the point to be measured, and calculating the refractive power from the spatial line frequency.

The invention permits a greater degree of accuracy and a higher degree of tolerance in quantitative measurements by permitting the points on the image corresponding to points on the anterior corneal surface to be measured relative to the central ray through the entrance pupil of the eye associated to the corneal surface. The process of determining the refractive power of a point is further optimized and simplified when the chief ray corresponds to an intersection point on the grid image. The rectilinear grid can be fabricated to be compatible with a wide variety of existing keratoscopes, and the method afforded by the use of the rectilinear grid element provides an accurate determination of the curvature of the anterior corneal surface.

For a fuller understanding of the nature and advantages of the invention, reference should be had to the ensuing detailed description taken in conjunction with the accompanying drawings.

DESCRIPTION OF THE PREFERRED EMBODIMENTS

Figure 1:
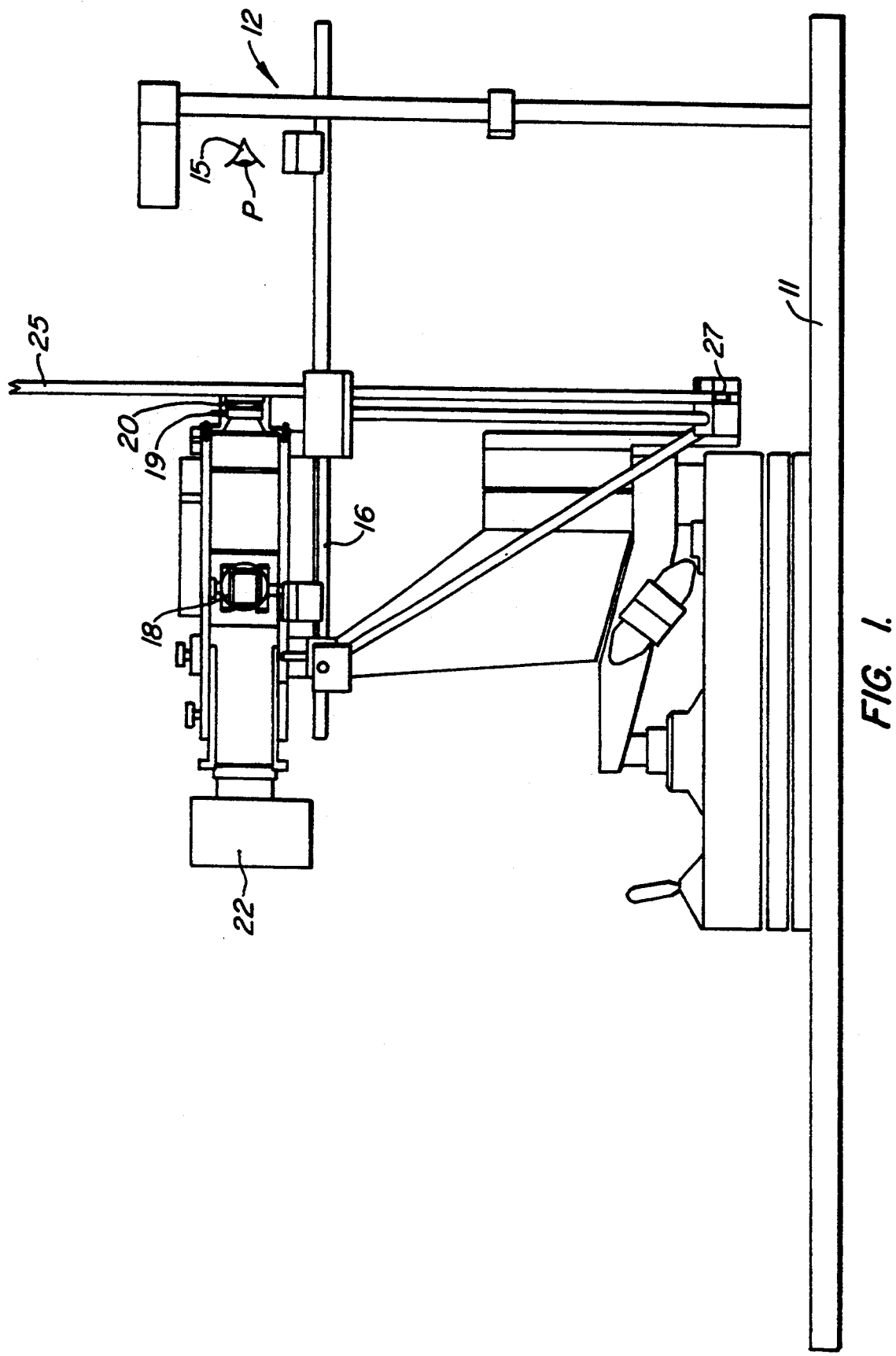
FIG. 1 is a schematic side view illustrating the preferred embodiment of the invention.
Figure 2:
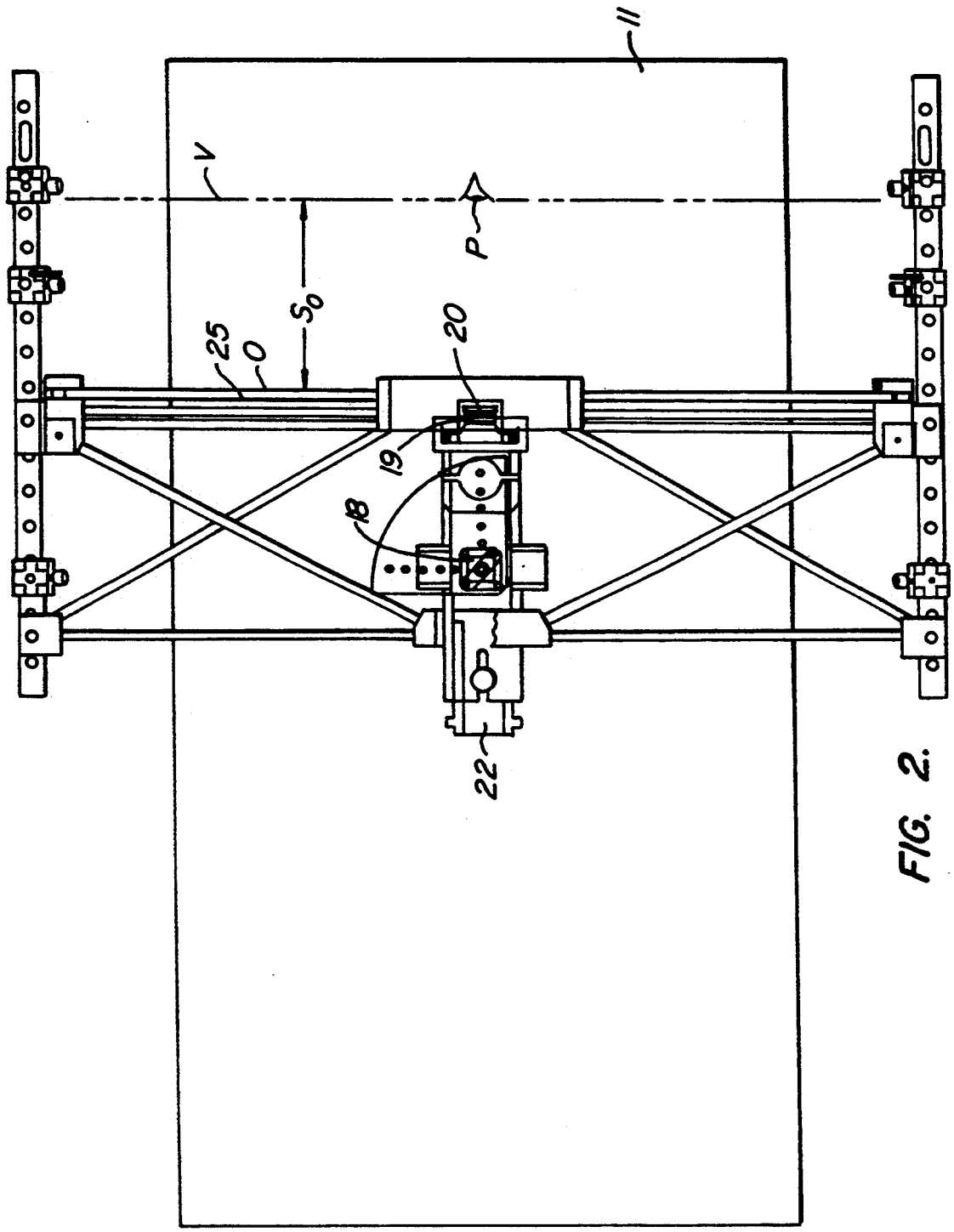
FIG. 2 is a top view of the embodiment of FIG. 1.

Turning now to the drawings, FIGS. 1 and 2 illustrate a photokeratoscope incorporating the preferred embodiment of the invention. As seen in these Figs., the optomechanical elements comprising the photokeratoscope are mounted on a base generally designated with reference numeral 11. These elements include a suitable patient station of known design generally designated with reference numeral 12 which is used to position the patient's eye 15 at a first planar position at axial reference point P. The plane in which reference point P is located is referred to herein as the vertex plane V which is ideally tangent to the forward most point on the anterior surface of the cornea of the eye 15. Mounted on a platform 16 is an optical apparatus including a beam splitter 18, an iris diaphragm 19, a focal lens 20 and a camera 22. The purpose of elements 18, 19, 20 and 22 is to properly align the eye 15 and to capture an image of a pattern reflected off the anterior corneal surface of the eye 15. Typically, alignment of the eye 15 is aided by the use of a fixation light (not shown) located at some point along the axis of the imaging system. For this purpose, a sheet 25 having the curvilinear pattern illustrated in FIG. 3 formed therein is mounted in a suitable holder 27 in a plane O which is a prescribed distance $S_0$ from the vertex plane V. The plane of sheet 25 is referred to herein as the object plane O.

Suitable illumination sources are provided for the apparatus of FIGS. 1 and 2 for the purpose of illuminating the anterior corneal surface of the eye 15 and also the curved grid pattern on sheet 25. Preferably, the light sources for both the eye 15 and the sheet 25 are separate flash sources which are briefly energized in order to capture a flash image on the film in camera 22. The light source to illuminate eye 15 is can be positioned between the sheet 25 and the vertex plane V; while the light source to illuminate the grid pattern on sheet 25 is preferably a flash lamp arranged to inject light into the interior of the sheet 25. Since such arrangements are known, further description is omitted to avoid prolixity.

Figure 3:
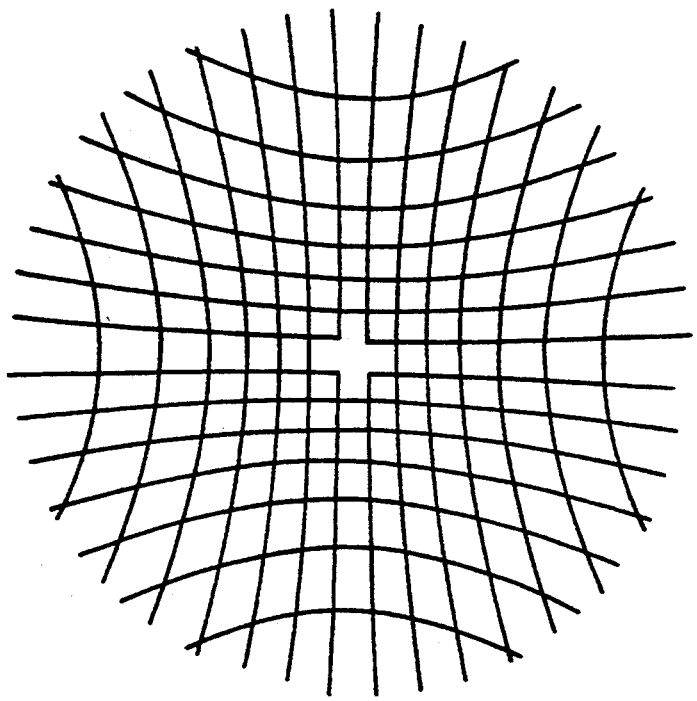
FIG. 3 is a plan view showing the grid used in the FIG. 1 embodiment.

With reference to FIG. 3, the pattern formed on sheet 25 consists of a plurality of mutually orthogonal essentially hyperbolic curved lines dimensioned and arranged with such a spatial frequency that the virtual image of the pattern when reflected from the anterior surface of the cornea of eye 15 and captured on the film in camera 22 will comprise a rectilinear grid if the reflecting surface is a spherical surface of radius lying within a predetermined range encompassing eyes usually encountered clinically. The individual curved lines in the grid of FIG. 3 can be patterned by selecting the value of the desired radius of curvature, the separation distance $S_0$ and the desired dimensional spacing between adjacent lines in the rectilinear grid pattern (i.e., the orthogonal distance between adjacent lines—assuming that the lines are equidistant, i.e., that the pattern is truly a grid). The pertinent transformation equations required to transform a rectilinear grid in plane V to the FIG. 3 grid in plane O are set forth in the appendix to this specification. In general, the transform for mapping a point in the plane V to a point in the plane O can be expressed in polar coordinates for the points in plane V. The actual pattern lines on sheet 25 are made by placing the blank sheet 25 into a computer numeric controlled milling machine, and forming the lines on the camera 22 side of the sheet 25, using the transformed values of points along the individual points on a given line of the rectilinear grid and connecting the transform point values. More specifically, a first set of parallel lines lying in two adjacent quadrants (i.e., the first and second quadrant in a cartesian coordinate system) is transformed into the curved line counterparts in the plane O. Next, these lines are rotated about the origin by: 90° to form a second set of lines, which are then transformed into the curved lines. This process is repeated until the complete curved line pattern shown in FIG. 3 results.

In the preferred embodiment of the pattern shown in FIG. 3, the pattern is centered about the origin without any lines occluding the entrance pupil of the camera 22. This frees the central area of the pattern to enable the camera operator to view the eye 15 coaxially through the origin of the pattern when aligning the apparatus prior to obtaining the reflected image. The grid on sheet 25 is completed by highlighting the lines formed in the camera side surface thereof, in particular by highlighting the curved grooves with white paint or some other suitable light scattering substance.

The invention can be used to calculate the refractive power of the anterior surface of the cornea in the following manner. The distance between two points on the pattern corresponds to the refractive power D (in diopters) between the two points. In particular, the refractive power can be determined from the equation:

$$D=(n-1)/R=A/X_i$$

where n is the index of refraction of the pertinent portion of the eye 15 (usually taken as the index of the aqueous humor with a value of 1.3375), R is the radius of curvature of the anterior surface of the cornea corresponding to the point being measured, A is a constant which can be determined using calibration spheres, and $X_i$ is the distance between the two points on the virtual image of the grid pattern. Thus, when a grid such as the grid shown in FIG. 3 is placed in front of the cornea and an image of the grid reflected from the anterior corneal surface (i.e., a catoptric image of the grid) is captured, that image may be quantitatively analyzed to compute the refractive power of any point on the corneal surface represented in the image. Most importantly, since the image of the pupil will also be captured on the film, the center of the pupil which corresponds to the chief ray (as opposed to the central reflex) can be used as the center of the grid system for computation purposes. When the chief ray coincides with the intersection of two lines on the grid in FIG. 3, then the distance between that intersecting point and any other point on the grid can be used to determine the refractive power of the anterior corneal surface at that other point. Where the chief ray is not coincident with the intersection of two lines on the image pattern, the value of the refractive power can still be readily calculated by simply interpolating between the four intersection points which define the rectilinear grid element enclosing the chief ray.

The process of calculating the corneal refractive power at each point relative to the chief ray can be accomplished using a transfer matrix. In particular, the value of the refractive power D can be expressed as:

$$D=af+b,$$

where a and b are regression coefficients and f is the spatial frequency of the grid lines. The spatial frequency of the grid lines is simply the number of lines per linear unit value (e.g., number of lines per ram).

By calibrating the imaging system to obtain the values of the regression coefficients, the refractive power of the corneal surface at a given point can be simply calculated using the above equation and substituting for the value f the quantity $$\delta t_r/\delta r$$

where $\delta t_r$ is the radial number of cycles between the chief ray and the point whose refractive power is to be measured, and $\delta r$ is the value of the radial distance between the two points on the captured image. The radial number of cycles is obtained by separately counting the number of grid lines $L_x$ along the horizontal axis and along the vertical axis $L_y$ and calculating $\delta t_r$ from the well-known Pythagorean relationship:

$$\delta t_r = [L_x^2 + L_y^2]^{\frac{1}{2}}$$

Figure 4:
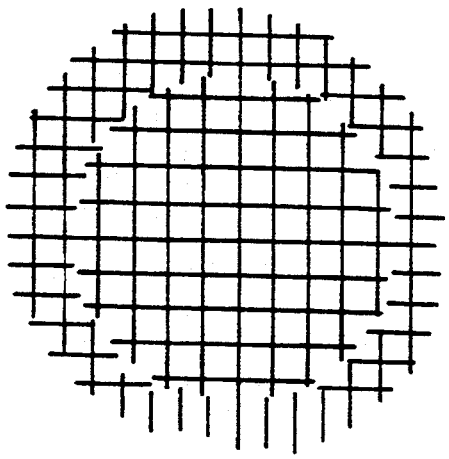
FIGS. 4 and 5 are images showing the FIG. 3 grid reflected from different surfaces.
Figure 5:
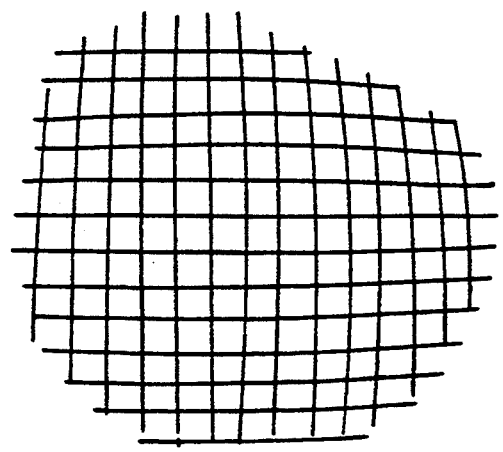

P The grid of FIG. 3 may also be used in a qualitative way to analyze the curvature of the anterior corneal surface. FIG. 4 is an image of a rectilinear grid from a bifocal anterior corneal surface with different radii of curvature consistent with a −8D correction on a 43D cornea as would be measured by conventional keratometry. As can be seen in FIG. 4, abrupt changes in curvature of the surface corresponding to the region between the two focal surfaces produce breaks in the lines of the grid. FIG. 5 illustrates the effect of gradual changes in the corneal surface curvature on the pattern of the grid lines. As seen in this Fig., which is a photograph of an eye approximately one month after photorefractive keratectomy to provide a −2.75D correction, the lines in the pattern image are essentially straight both centrally and peripherally but bend near the edge of the treatment. This observable bending is consistent with the concept of a transition zone in which corneal healing gently attenuates the laser treatment peripherally.

As will now be apparent, a rectilinear photokeratoscope fabricated in accordance with the teachings of the invention can be used to evaluate a wide variety of features associated with corneal curvature, including the centration of refractive surgeries, the monitoring of corneal healing, and the determination of refractive power. In addition, the invention can be used to provide information to improve the surface contact between the anterior surface of the cornea and the posterior surface of a contact lens. Moreover, the sheet-like grid is readily adaptable for use with a wide variety of existing keratoscopic installations and thus provides a powerful supplemental tool for studying the curvature and refraction of the anterior surface of the cornea.

As noted above, the grid element contains a grid pattern which results in a rectilinear grid image if the reflecting surface is a spherical surface of radius lying within a predetermined range. The radius of curvature used to prepare the pattern on sheet 25 in the preferred embodiment was that calculated from a cornea having a refractive power of 43 D, assuming an index of refraction n=1.3375. With this grid pattern, it was empirically determined that the reflected image is a rectilinear grid over a range of corneas of different measurable refractive powers (and thus different radii of curvature). Consequently, for most human eyes a single grid element 25 will provide the desired results. As will be apparent to those skilled in the art, other patterns using different assumptions about the sphericity or other curvature of the anterior corneal surface may be prepared according to the principles of the invention. Also, while the grid element in a preferred embodiment has been described as a flat sheet 25 having the pattern engraved on one side thereof, other configurations are possible. For example, the pattern may be formed internally of a flat sheet, e.g., by preparing a laminated multi-layer sheet. Similarly, other geometries than a flat planar geometry may be used, depending on the nature of the associated optical apparatus. Thus, grid elements in the shape of a cone or a cylinder having the pattern formed on an appropriate surface can also be employed (e.g., such as the cylindrical inner surface shown on the keratoscope cone assembly 10 in the U.S. Pat. No. 4,863,260 cited above). In addition, while the pattern has been specifically described and illustrated as sets of intersecting curved lines, in some applications the pattern may assume the form of points corresponding to the intersections of the lines. In such applications, the points can be calculated and then formed in the element, such as flat sheet 25.

While the above provides a full and complete description of the preferred embodiments of the invention, various modifications, alternate constructions and equivalents will occur to those skilled in the art. For example, other optical and optomechanical configurations may be employed, as desired. In addition, the index of refraction n used in the preparation of the grid element pattern may vary, depending on the particular intended application. For an eye 15 having undergone some refractive surgeries, e.g., the value of n can be that of the cornea, viz. 1.377. Therefore, the above should not be construed as limiting the invention, which is defined by the appended claims.

What is claimed is:

1. A method of determining the refractive power of a point on the anterior corneal surface of an eye, said method comprising the steps of:

capturing an image of a grid reflected from the anterior surface of the cornea, the grid having intersecting lines arranged in a pattern which forms a substantially rectilinear grid when reflected from a curved surface having a radius of curvature lying within a predetermined range;

measuring the spatial frequency f of grid lines between the reference point corresponding to the chief ray of the pupil of the eye and the point whose refractive power is to measured; and calculating the refractive power from the relationship $D = af + b$, where a and b are predetermined constant values.

2. The method of claim 1 wherein the reference point corresponding to the chief ray of the pupil comprises an intersection point of two grid lines.

3. A method of determining the refractive power of a location on the anterior corneal surface of an eye, said method comprising the steps of:

(a) capturing an image of a pattern reflected from the anterior surface of the cornea, the pattern having an array of points which forms a substantially rectilinear array of points when reflected from a curved surface having a curvature lying within a predetermined range;

(b) measuring the spatial frequency f of lines drawn between adjacent points on the pattern image, the spatial frequency f being measured from a reference location to a location on the image corresponding to the location on the corneal surface to be measured, the reference location corresponding to the chief ray of the pupil of the eye; and (c) calculating the refractive power from the relationship $D = af + b$, where a and b are predetermined constant values.

4. The method of claim 3 wherein the reference location corresponding to the chief ray of the pupil of the eye comprises one of the points on the image.

5. A method of determining the curvature of a corneal surface, said method comprising the steps of:
   (a) providing a grid of intersecting lines having a pattern which forms an image comprising a substantially rectangular grid when reflected from a curved surface having a radius of curvature lying within a predetermined range;
   (b) placing the grid before the eye;
   (c) capturing the image of the grid reflected from the corneal surface; and
   (d) determining the refractive power of a point on the corneal surface from the image obtained in step (c) by measuring the spatial frequency f of grid lines between a reference point and the point to be measured, and calculating the refractive power from the relationship $D = af + b$, where a and b are predetermined constant values.

6. The method of claim 5 wherein said step of measuring includes the steps of determining the point on the image corresponding to the chief ray of the pupil associated to the corneal surface, and selecting this point as the reference point.

7. A method of determining the curvature of a corneal surface, said method comprising the steps of:
   (a) providing an imaging element of points having a pattern which forms an image comprising a substantially rectilinear array of points when reflected from a curved surface having a curvature lying within a predetermined range;
   (b) placing the imaging element before the eye;
   (c) capturing the image of the pattern reflected from the anterior corneal surface; and
   (d) determining the refractive power of a location of interest on the corneal surface from the image obtained in step (c) by measuring the spatial frequency f of lines extending between adjacent points on the pattern image, the spatial frequency being measured from a reference location to the location corresponding to the location on the corneal surface to be measured, and calculating the refractive power from the relationship $D = af + b$, where a and b are predetermined constant values.

8. The method of claim 7, wherein said step of measuring includes the steps of determining the location on the image corresponding to the chief ray of the pupil associated to the corneal surface, and selecting this location as the referencelocation.

* * * * *